US00PP34911P3

(12) United States Plant Patent
Conev et al.

(10) Patent No.: US PP34,911 P3
(45) Date of Patent: Jan. 17, 2023

(54) SHRUB ROSE PLANT NAMED 'VLR003'

(50) Latin Name: *Rosa hybrida*
Varietal Denomination: VLR003

(71) Applicants: Vineland Research and Innovation Centre, Ontario (CA); Canadian Nursery Landscape Association, Ontario (CA)

(72) Inventors: Rumen Conev, St. Catharines (CA); Parminderjit Sandhu, Kitchener (CA)

(73) Assignees: VINELAND RESEARCH AND INNOVATION CENTRE, Vineland Station (CA); CANADIAN NURSERY LANDSCAPE ASSOCIATION, Milton (CA)

( * ) Notice: Subject to any disclaimer, the term of this patent is extended or adjusted under 35 U.S.C. 154(b) by 0 days.

(21) Appl. No.: 17/688,027

(22) Filed: Mar. 7, 2022

(65) Prior Publication Data

US 2022/0287213 P1 Sep. 8, 2022

(30) Foreign Application Priority Data

Mar. 8, 2021 (CA) ..... PBR 21-10444

(51) Int. Cl.
*A01H 5/02* (2018.01)
*A01H 6/74* (2018.01)

(52) U.S. Cl.
USPC ..... Plt./104
CPC ..... *A01H 6/749* (2018.05)

(58) Field of Classification Search
USPC ..... Plt./104
CPC ..... A01H 5/0222
See application file for complete search history.

(56) References Cited

U.S. PATENT DOCUMENTS

PP16,659 P2 6/2006 Lim
PP24,195 P2 1/2014 Kordes

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

A new and distinct variety of shrub rose plant, referred to by its cultivar name, 'VLR003', is described. The new variety forms on a continuous basis attractive, yellow-colored double flowers from spring to fall. The growth habit is semi-upright compact bush. Attractive semi-glossy, dark green foliage is formed. The new variety is cold hardy. Additionally, the new variety is particularly well suited for growing as distinctive ornamentation in the landscape.

5 Drawing Sheets

Figure 1:
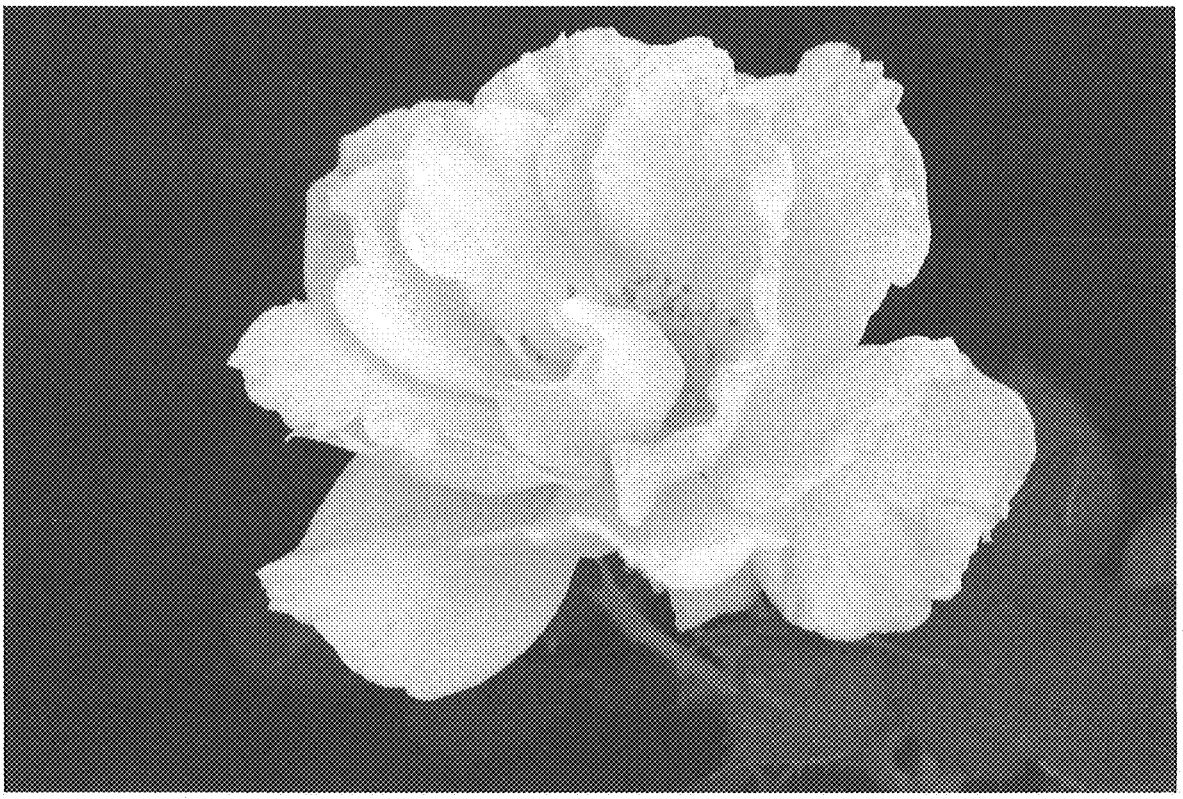

Latin name of genus and species of plant claimed: *Rosa hybrida.*

Variety denomination: 'VLR003'.

CROSS REFERENCE TO RELATED APPLICATIONS

This application claims priority to Plant Breeders' Right Application Number 21-10444, which was filed in Canada on Mar. 8, 2021, the contents of which are hereby incorporated by reference for all purposes.

BACKGROUND OF THE INVENTION

The new variety of shrub rose plant of the present invention was created by controlled breeding in May 2011 in Vineland Station, Ontario, Canada by artificial pollination wherein two parents were crossed which previously had been studied in the hope that they would contribute to the desired traits. The female parent (i.e., the seed parent) of the new variety was 'BAline' (U.S. Plant Pat. No. 16,659). The male parent (i.e., the pollen parent) of the new variety was '282' (non-patented).

The parentage of the new variety can be summarized as follows:

'BAline' × '282'

The seeds resulting from the above pollination were sown and small plants were obtained which were physically and biologically different from each other. Selective study resulted in the identification of a single plant of the new variety.

The new variety has been found to undergo asexual propagation at Vineland Station, Ontario, Canada by vegetative cuttings. Asexual propagation techniques in Vineland Station, Ontario, Canada, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of shrub rose plant of the present invention possesses the following combination of characteristics:

(a) continuously forms attractive, yellow-colored double petal flowers,
(b) exhibits a semi-upright compact bush growth habit, and
(c) forms attractive ornamental semi-glossy, dark green colored foliage.

The new variety well meets the needs of the horticultural industry. It can be grown to advantage as attractive ornamentation in parks, gardens, public areas, and residential landscapes. Accordingly, it is particularly well suited for growing in the landscape.

The new variety can be readily distinguished from its ancestors. More specifically, 'BAline' (i.e., the seed parent) displays more petals per flower (approximately 32 petals on average) compared to the new variety (approximately 17 petals on average). Additionally, '282' (i.e., the pollen parent) displays less petals per flower (approximately 11 petals on average) compared to the new variety (approximately 17 petals on average). Moreover, the new variety can be readily distinguished from non-parental related similar varieties. For example, 'KORfizzlem' (U.S. Plant Pat. No. 24,195) displays less petals, exhibits larger leaflets, and is a larger plant compared to the new variety.

The new variety has been named 'VLR003'. The trademark name for the new variety is YUKON SUN™.

The new variety has not been sold or offered for sale as of March 2022.

BRIEF DESCRIPTION OF THE PHOTOGRAPHS

The accompanying photographs show, as nearly true as it is reasonably possible to make the same in a color illustration of this character, typical specimens of the new variety. The illustrated rose plants of the new variety were approximately two-years-old and were grown outdoors during the spring and summer of 2020 and 2021 in three-gallon containers on their own roots at Vineland Station, Ontario, Canada.

FIG. 1—illustrates a specimen of an opened flower.

Figure 2:
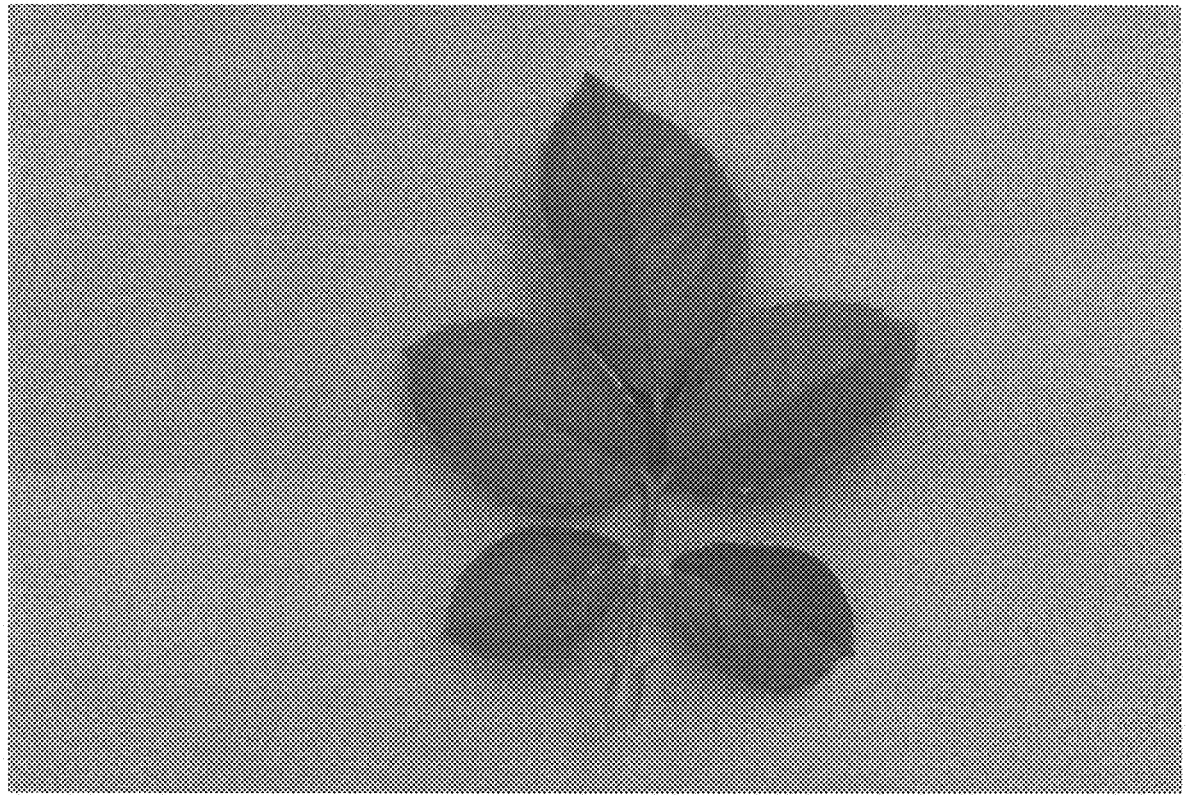

FIG. 2—illustrates a specimen of a 5-leaflet leaf.

Figure 3:
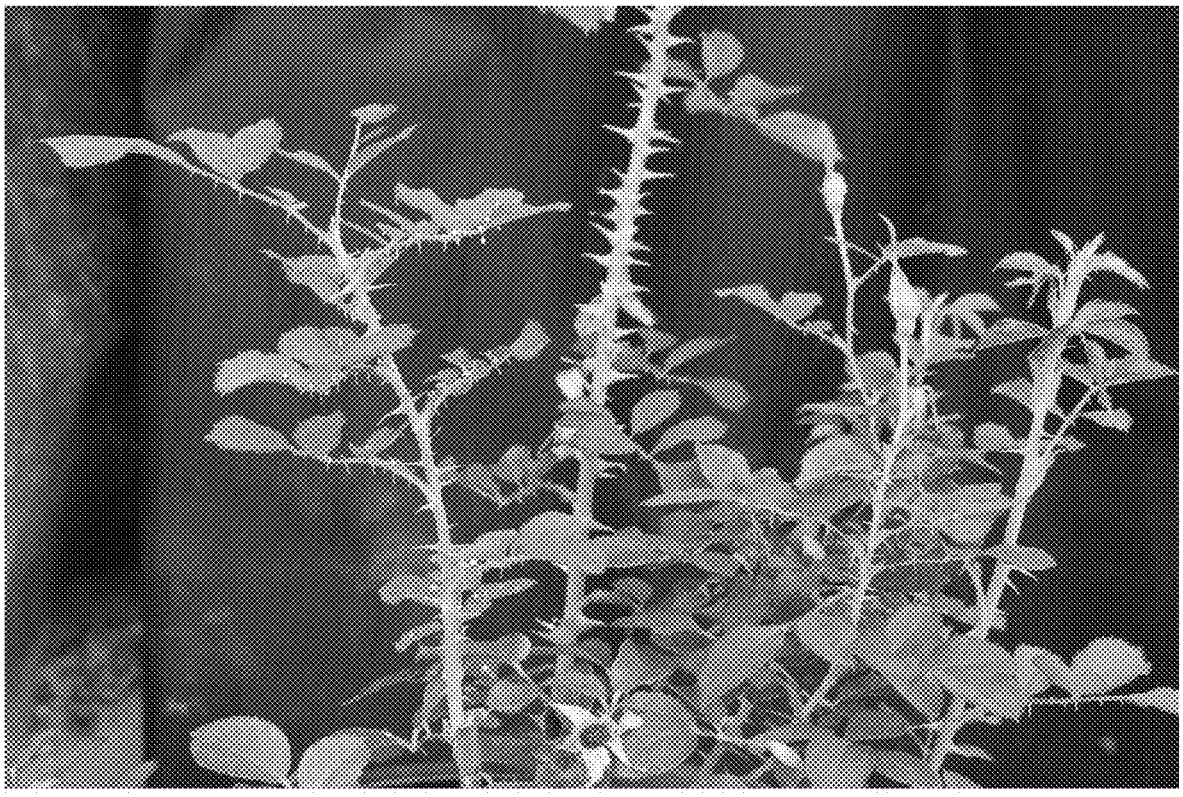

FIG. 3—illustrates specimen of young shoots.

Figure 4:
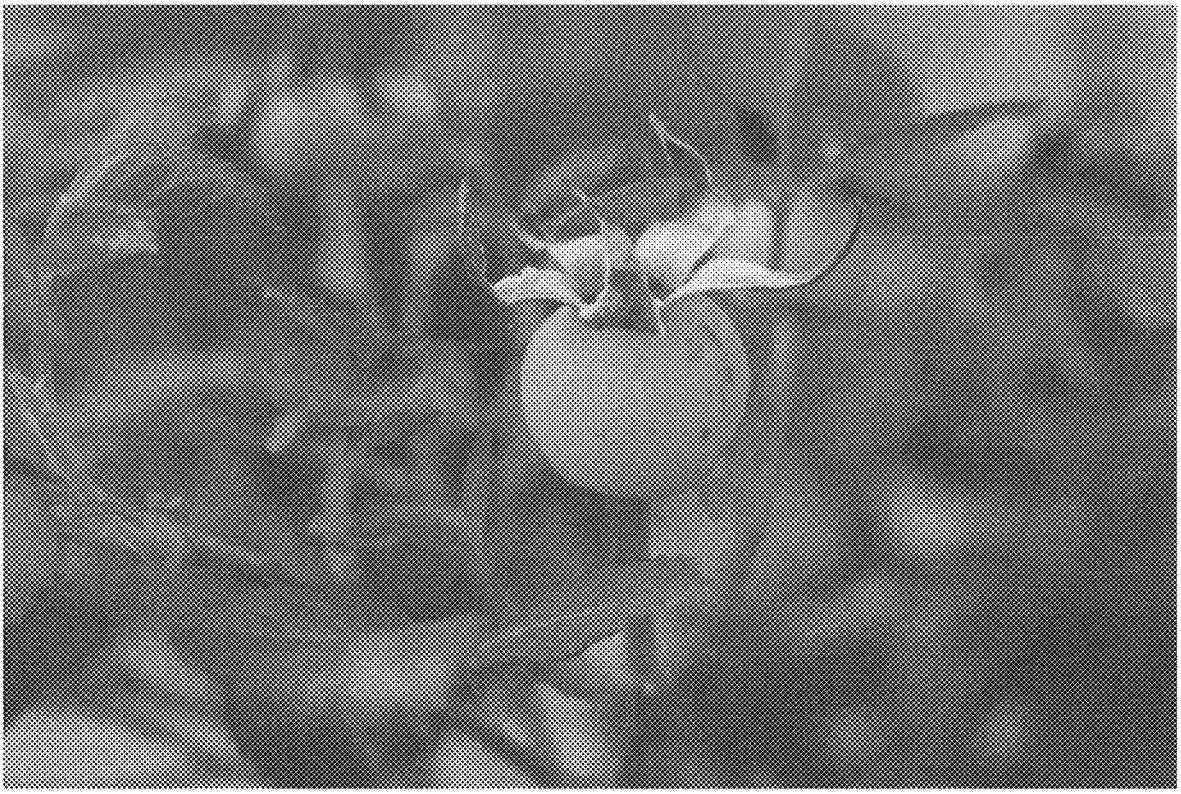

FIG. 4—illustrates specimen of hips.

Figure 5:
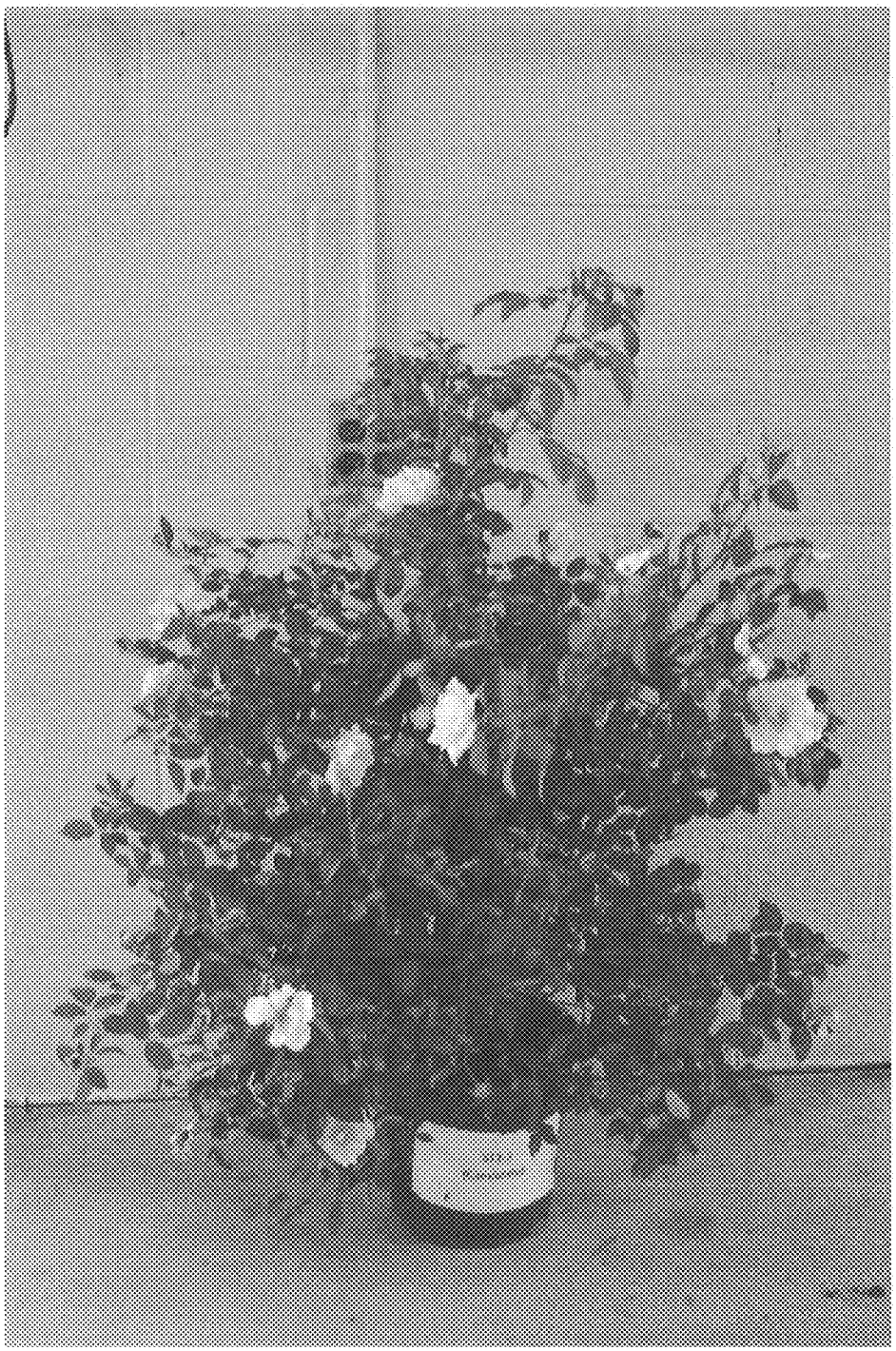

FIG. 5—Illustrates a specimen of the plant displaying opened flowers.

DETAILED BOTANICAL DESCRIPTION

The chart used in the identification of colors is that of The Royal Horticultural Society (R.H.S. Colour Chart, 2007 edition). The terminology which precedes reference to the chart has been added to indicate the corresponding color in more common terms. The description is based on a two-years-old specimen of the new variety, observed during August, while growing on its own roots outdoors in a three-gallon container in Vineland Station, Ontario, Canada.

Botanical classification: *Rosa hybrida* cultivar VLR003.

Plant:

*Height*.—Approximately up to 86.0 cm.

*Width*.—Approximately up to 83.0 cm.

*Habit*.—Semi-upright, compact, bush.

Branches:

*Stem color*.—Old wood: commonly near Greyed-Orange Group 177B. Young stems: commonly near Green Group 138B.

*Length*.—Main stems: approximately 81.0 cm on average. Secondary stems: approximately 64.0 cm on average.

*Diameter*.—Main stems: approximately 8.6 mm on average. Secondary stems: approximately 5.4 mm on average.

*Thorns*.—Amount: approximately 3.5 per internode. Young thorns: length is approximately 9.0 mm on average; width is approximately 4.0 mm at base; color is commonly near Red-Purple Group 63C. Old thorns: length is approximately 11.0 mm on average, width is approximately 4.0 mm at base; color is commonly near Greyed-Orange Group 167D.

*Young shoots*.—Anthocyanin coloration: commonly near Greyed-Purple Group 187C.

Leaflets:

*Number*.—Predominantly 5.

*Shape*.—Elliptic; apex shape is acute; base shape is obtuse.

*Margin*.—Serrate with sub-teeth.

*Undulation*.—Intensity of margin undulation is moderate.

*Texture*.—Upper surface: smooth. Under surface: smooth.

*Intensity of glossiness of upper surface*.—Medium.

*Size*.—Terminal leaflet: length is approximately 5.1 cm on average; width is approximately 3.3 cm on average. Lower leaflets: length is approximately 3.8 cm on average; width is approximately 2.8 cm on average. 5-Leaflet leaf: length is approximately 10.2 cm on average; width is approximately 8.1 cm on average.

Foliage:

*Young foliage*.—Upper surface color: commonly near Orange-Red Group N34A. Under surface color: commonly near Green Group 138B.

*Mature foliage*.—Upper surface color: commonly near Green Group N137B. Under surface color: commonly near Green Group 138B.

*Venation*.—Pattern: cross-venulate. Color: upper and under surfaces are commonly near Green Group 138B.

*Petiole*.—Texture: upper surface is rough; under surface is rough. Length: approximately 21.0 mm on average. Diameter: approximately 1.3 mm on average. Upper surface color: commonly near Green Group 138A. Under surface color: commonly near Green Group 138B.

*Petiolule*.—Length: approximately 2.0 mm on average. Diameter: approximately 1.25 mm on average. Texture: hairy. Color: commonly near Green Group 138B.

*Rachis*.—Diameter: approximately 2.2 mm on average. Texture: smooth. Color: commonly near Green Group 138C.

Inflorescence:

*Number of flowers*.—About 130 blooms on average on a plant at once.

*Number of blossoms per stem or in a cluster*.—Typically, 1 bloom on average.

*Blooming season*.—Typically, in bloom outdoors from June to October in Vineland Station, Ontario, Canada.

*Peduncle*.—Color: commonly near Green Group 138B. Width: approximately 2.0 mm on average. Length: approximately 2.9 cm on average. Texture: smooth.

*Sepals*.—Number: 5. Upper surface color: commonly near Green Group 143C. Under surface color: commonly near Green Group 143A. Size: length is approximately 1.6 cm on average; width is approximately 5.0 mm on average. Shape: lanceolate; apex is acicular. Margin: ciliate. Texture: hairy.

*Buds*.—Shape: elliptical. Size: length is approximately 2.0 cm on average; width is approximately 9.0 mm on average. Color: commonly near Green Group 138B.

*Flower*.—Type: double. Diameter: approximately 7.5 cm on average. Depth: approximately 2.6 cm on average. Duration: on the plant approximately 4 days. Petal color when opening: upper surface is commonly near Yellow Group 10A; under surface is commonly near Yellow Group 10A. Petal color when fully open: upper surface is commonly near Yellow Group 8B; under surface is commonly near Yellow Group 8B.

*Fragrance*.—Mild.

*Petal*.—Number 17. Drop: good, clean. Shape: obovate; apex is obtuse; base is acute. Margin: undulate. Texture: smooth.

*Stamen*.—Number: approximately 56. Anthers: color is commonly near Orange Group 24B; length is approximately 1.8 mm; width is approximately 0.8 mm; shape is sagittate. Filaments: length is approximately 9.0 mm on average; diameter is approximately 0.28 mm; color is commonly near Yellow-Orange Group 14B.

*Pistils*.—Number: approximately 41. Style: length is approximately 4.0 mm; diameter is approximately 0.35 mm; color is commonly near Red-Purple Group 59C. Stigma: length is approximately 0.9 mm; width is approximately 0.7 mm; shape is irregular round; color is commonly near Yellow-Orange Group 23B.

*Receptacle*.—Size: length is approximately 9.0 mm; width is approximately 7.0 mm. Shape: pitcher shaped. Color: commonly near Green Group 138B.

*Pollen*.—Color: commonly near Yellow-Orange Group 16D. Amount: good.

*Hips*.—Color: commonly near Orange Group 25B. Diameter: approximately 13.0 mm.

*Seeds*.—Color: commonly near Yellow Group 11D. Diameter: approximately 3.0 mm.

Development:

*Vegetation*.—Semi-glossy and dark green.

*Blossoming*.—Continuous from spring to fall.

*Resistance to diseases*.—Good resistance to black spot disease caused by *Diplocarpon rosae*.

*Hardiness*.—Cold hardy to USDA Zone 4A.

The new 'VLR003' variety has not been observed under all possible environmental conditions to date. Accordingly, it is possible that the phenotypic expression may vary somewhat with changes in light intensity and duration, cultural practices, and other environmental conditions.

We claim:

1. A new and distinct variety of shrub rose plant named 'VLR003' characterized by the following combination of characteristics:

(a) continuously forms attractive, yellow-colored double petal flowers, (b) exhibits a semi-upright compact bush growth habit, and (c) forms attractive ornamental semi-glossy, dark green colored foliage;

substantially as herein shown and described.

* * * * *